United States Patent
Selker et al.

(10) Patent No.: US 9,921,576 B2
(45) Date of Patent: Mar. 20, 2018

(54) VIRTUAL TRANSMITTER FOR BIOREACTOR AUTOMATION SYSTEM

(75) Inventors: Mark Selker, Los Altos Hills, CA (US); Barbara Paldus, Woodside, CA (US)

(73) Assignee: Finesse Solutions, Inc., Santa Clara, CA (US)

( * ) Notice: Subject to any disclaimer, the term of this patent is extended or adjusted under 35 U.S.C. 154(b) by 1578 days.

(21) Appl. No.: 12/151,254

(22) Filed: May 5, 2008

(65) Prior Publication Data

US 2011/0060463 A1    Mar. 10, 2011

(51) Int. Cl.
  *G05B 21/00*  (2006.01)
  *G05B 23/02*  (2006.01)
  *C12M 1/36*  (2006.01)

(52) U.S. Cl.
  CPC ......... *G05B 23/0221* (2013.01); *C12M 41/48* (2013.01)

(58) Field of Classification Search
  CPC .. G01N 21/783; G01N 21/80; G01N 21/8507; H01S 5/06804; G05B 23/0221
  USPC ........................................................ 700/266
  See application file for complete search history.

(56) References Cited

U.S. PATENT DOCUMENTS

| | | | |
|---|---|---|---|
| 7,867,752 B1 * | 1/2011 | Greenberger et al. | 435/286.1 |
| 2005/0154129 A1 * | 7/2005 | Battiste | 525/74 |
| 2005/0158701 A1 * | 7/2005 | West | 435/3 |

OTHER PUBLICATIONS

Emerson Process Management and Rosemount Analytical Manual, "RDO® Optical Dissolved Oxygen Analyzer and Sensor,"(Nov. 2013), 32 pp.
Broadley Technologies, "Instruction Manual: Model 30 pH/Dissolved Oxygen Dual Input 4-Wire Transmitter," (Jun. 2001), 69 pp.

* cited by examiner

*Primary Examiner* — Dean Kwak
(74) *Attorney, Agent, or Firm* — Weaver Austin Villeneuve & Sampson LLP

(57) ABSTRACT

A bioreactor monitoring and/or control system utilizing only non-dedicated user input and information display devices, a digital controller and software, which system comprises:
i) at least one diagnostic probe for measuring operating conditions in a bioreactor;
ii) signal conditioning and communication electronics which supply operating current and/or voltage to the probe and which convert the diagnostic signal into a format accessible by a digital controller which directly receives the format converted signal and transmits it to software which enables the display device to show the converted signal, and also instruct the controller to implement changes in the operating conditions in the reactor, and
iii) a software-based virtual transmitter which substantially replicates the keyboard, display, menu-tree and response of a physical sensor transmitter.

14 Claims, 21 Drawing Sheets

Dissolved Oxygen 2 Point Calibration

Review Previous Calibration for this probe. Press NEXT to continue when review is complete.

Manufacturer: Finesse
Serial Number: 123456

| Date | Vessel | Temp | Zero nA | Span nA | Span DO | Slope | Cal By |
|---|---|---|---|---|---|---|---|
| 8/4/2006 1:41:18 PM | V1 | 25.7 | 0.01 | 80 | 100 %Sat | 0.8nA/nA | RWarren |
| 8/4/2006 3:06:22 PM | V1 | 25.7 | 0.01 | 80 | 100 %Sat | 0.8nA/nA | RWarren |
| 8/4/2006 3:12:06 PM | V1 | 25.7 | 0.01 | 80 | 100 %Sat | 0.8nA/nA | RWarren |

[Next] [Cancel]

VIRTUAL TRANSMITTER FOR BIOREACTOR AUTOMATION SYSTEM

FIELD OF THE INVENTION

This invention relates to a novel design for visualizing segments of a bioreactor monitoring and control system that is implemented in software, rather than hardware (i.e., a "virtual" system. A preferred application of this virtual system is in the control of a bioprocess, such as cell culture or fermentation.

BACKGROUND OF THE INVENTION

The production of biotech drugs, pharmaceuticals, neutraceuticals, bio-diesel fuel, as well as many foods and beverages utilizes live cell cultures to implement a biochemical growth process. Optimization of this process during manufacturing requires the ability to control the environment in the bioreactor by detecting a multitude of process variables and controlling their values to be within a specified range of tolerances. Real-time monitoring of these variables and calculations based on these values are performed in order to determine the efficacy of the bioprocess underway.

Recently, systems for controlling process variables applicable to a bioprocess have become increasingly sophisticated. These systems frequently employ digital systems such as programmable logic chips (PLCs), micro-processor based software control systems, or a hybrid arrangement. Advancements in processors, communication hardware, protocols and archival software systems have transformed the concept of data management during bio-processing from a luxury to a necessity. The advent of sophisticated digital systems has given the bio-process engineer the capability to repeatedly apply the same complex series of actions to any bio-process. This has enabled large molecule pharmaceutical manufacturing to move towards the level of reproducibility that semiconductor processing now enjoys. Additionally, the use of digital systems to implement supervisory control and data acquisition (SCADA) now allows a smoother path to satisfying the requirements of good manufacturing process (GMP) doctrines as well as US Food and Drug Administration (USFDA) requirements. However, as capabilities have expanded so have the costs; yet for fully automated control systems and data histories to become commonplace in the biotech industry these process control systems need to be affordable and accessible to even the smallest biotech manufacturing organizations. One route to containing costs is to minimize functional redundancy in the automated process monitoring and control systems.

Irrespective of the complexity of the automation system, each of these control and monitoring platforms for a bioreactor share some degree of commonality. The common elements include a human-machine interface (HMI), a controller, internal and network communications interfaces, instruments by which to measure data from sensors within the bioreactor or adjoining process equipment, and actuators by which to physically interface to process equipment such as agitators, valves, pumps, mass flow controllers (MFCs) and/or rotameters.

A prior art system is shown schematically in FIG. 1:
1.1 is the HMI,
1.2 is a unit that contains the controller and network communications interfaces,
1.3 is a utility tower unit that contains sensor transmitters, relays, and analog outputs for actuator control, as well as electronics that aggregate and condition communications from both transmitters and actuators,
1.4 is a materials handling unit for gases and/or liquids that contains pumps and MFCs,
1.5 is a first bioreactor and,
1.6 is a second bioreactor also coupled to utility tower 1.3

Optionally, additional utility towers, pumps and bioreactors (3 and 4) can be operably connected to the same controller and HMI as shown. Note that this architecture can be implemented using either an aggregated design where all of the components of bioreactor units 1 through 4 are packaged in a single enclosure that can control multiple bioreactors (e.g., FIG. 2a, shows an Applikon i-Control unit for control of two bioreactors, where 2.1 is the HMI, 2.2 is a set of integrated pumps, and 2.3 shows two banks of rotameters and FIG. 2b shows several i-Control units in a network).

Alternatively, amodular design with multiple enclosures is possible e.g., as shown in FIGS. 3a and 3b, which illustrates a Finesse TruViu RDPD automation system where 3.1 is the HMI, 3.2 is the utility tower, 3.3 is the pump tower, and 3.4 is the MFC unit). The optimal design employed by the end user is influenced by cost, space, maintenance, and ease-of-use requirements for each particular bio-process application. In general, a modular approach offers the greatest flexibility to the end user.

A personal computer (PC) is often used as a terminal or interface through which to access the automation controller and software. The HMI can be a monitor and keyboard that are directly attached to the PC or a separate touch screen display connected using a wireless device. If the PC is used as a terminal, the software values and instructions can reside there, and any executable code is downloaded to the controller where it runs independently of the PC. In cost sensitive applications such as research facilities, where process down-time is less of an issue, the controller can be directly implemented in the PC, whereas in applications requiring high up-time, the controller is often implemented as a separate device to enhance the reliability of the system. The separate controller either has available, or alternatively is packaged with, communications ports for communication with an external network in order to send and receive user commands, instructions, and/or new executable code.

FIG. 4 shows a schematic of a typical utility tower implementation. The utility tower is an enclosure housing the transmitters for the sensors/probes used in a bioprocess. Possible sensors include those which measure:
1. pH,
2. Dissolved oxygen,
3. Pressure,
4. Temperature,
5. Foam level,
6. Liquid level,
7. Weight,
8. Agitator motor speed and/or rocking period and angle,
9. Pump motor speed or number of revolutions, and
10. Gas flow rate In general all of these sensors will not utilize the same communication protocol. Some sensors output their signal as a 4 mA to 20 mA analog current, others use HART while still others use ModBus, (trade mark of Gould Inc.) ProfiBus, FieldBus, DeviceNet (trade mark of Device Net Vendor Assoc.), Ethernet, wired serial protocols such as RS-232 or RS-485 or wireless such as Bluetooth (trade mark of Bluetooth SIG. Inc.) or 802.15 or WiFi 802.11g. Some sensors use proprietary communication protocols developed by their manufacturer. In order to efficiently send signals to the controller, all or at least most of these sensor signals must be transformed into a common protocol and then aggregated in the utility tower. The aggregated communication line often employs serial communications using a bus. There are many digital bus communication protocols including, but not limited to, ModBus, ProfiBus, DeviceNet, and FieldBus.

FIG. 4 shows a typical prior art utility tower in which 4.1 is a pH transmitter, 4.2 is a dissolved oxygen transmitter, and 4.3 is the communication between these transmitters and their associated sensors, respectively, and 4.4 is the communication between these transmitters and the signal translator. These transmitters often use a HART protocol and therefore need to be sent through a device 4.5 that will translate the HART signals into a suitable Bus protocol, such as ModBus. The signals are then sent to a main signal aggregator 4.6. Many of the other analog or digital signals come in on lines 4.7 from the bioreactor. The pump and MFC towers are conditioned (translated) and aggregated in a separate component 4.8. These signals are then sent on their own line 4.9 to the main signal aggregator 4.6. The totality of the aggregated signals 4.10 is sent to the control tower, to be received by the serial input device. Note that several aggregators and translators can be sequenced, in order to expand the capacity and capability of the overall utility tower system.

Current practice calls for the sensor to connect to the bio-process SCADA system via a transmitter. A typical dissolved oxygen or pH transmitter is shown schematically in FIG. 5 where 5.1 is the transmitter enclosure, 5.2 is the display, 5.3 is the data entry keypad, 5.4 is the cable to the sensor/probe, 5.5 is the sensor/probe, and 5.6 is a data line output from the transmitter that carries the process variable information (and in some cases, additional diagnostic information and/or secondary/tertiary process variables). This data line can be a 4-20 mA analog or HART signal that is physically carried on 2 wires and carries information about the oxygen concentration or pH measured by the probe/transmitter pair. The output signal can also be encoded using a variety of digital protocols (e.g., RS-232, RS-485 etc.) with the value of the process variable contained therein. A transmitter is typically mounted inside a utility (or transmitter) tower, where its output signal is usually aggregated with that of other transmitters and/or actuators, and is sent to the control unit by the signal pathway described previously and illustrated in FIG. 4.

In this scenario, the power (e.g., 24 V DC) to the transmitter is provided by the utility tower, the power to the sensor is provided by the transmitter, and the signal from the sensor is received and conditioned by the transmitter. For transmitters having digital communications capability, i.e., more than just a 4 to 20 mA output signal, the transmitter is subservient to the automation system; namely, the user inputs a command through the automation system's HMI and the sensor transmitter reacts accordingly.

For instance, a typical polarographic dissolved oxygen transmitter or electrochemical pH sensor transmitter will allow the probe to be calibrated and then provide the calibrated probe signal as an output. In this scenario, the transmitter performs these tasks in response to commands sent by the bioprocess automation system. Additionally, as shown in FIG. 4 or FIG. 5, a transmitter with a microprocessor can transmit both the conditioned signal as well as raw signals from the probe. Specifically, digital transmitters are capable of transmitting to the bio-process automation system, both the signals with stored calibrations applied to them, as well as the raw signals (voltage or current or impedance) coming to the transmitters directly from the probes. The raw signals from the probe are important as they can be used in a diagnostic or troubleshooting capacity. For instance, with a pH probe, the raw output signal is the voltage (mV) developed in accord with the Nernst equation. This raw voltage, when monitored over time, can give insight into the probe's performance (e.g., output range, drift, etc.); additionally the impedance of the probe is indicative of its health (e.g., if the impedance rapidly drops to zero, a probe failure has occurred, and probe output should no longer be trusted as an accurate measurement of pH).

Similar output and diagnostic signals are available from multiple sensors. It should be noted that although these signals are sometimes accessible on the transmitter's display, they are often difficult or impossible to access in a typical bio-process automation system. Similarly, in many inexpensive bio-process automation systems, only the primary process variable from a sensor is measured and converted into a digitized form by proprietary electronics, so that the diagnostic information from raw signal values and/or secondary sensor signals are lost.

BRIEF DESCRIPTION OF THE DRAWINGS

FIG. 7b shows a typical face plate (for dissolve oxygen) that would be opened on 7a.

FIG. 7d shows a calibration face plate which would be opened on sensor page 7c.

DESCRIPTION OF THE INVENTION

Figure 1:
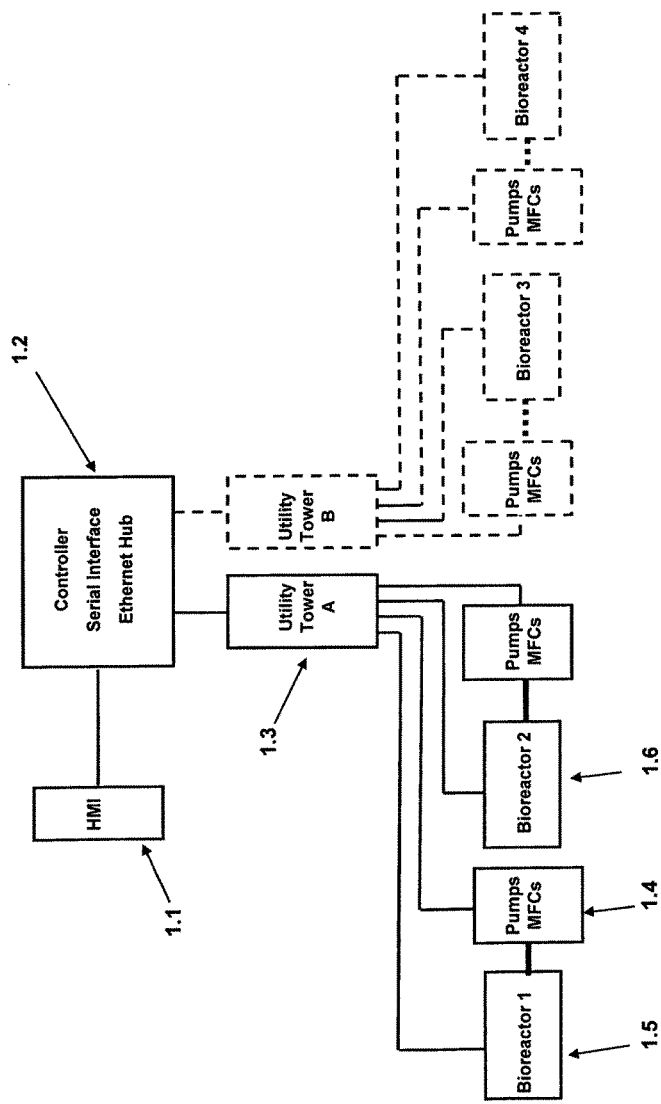
FIG. 1 shows a typical prior art architecture for a bioprocess control system where the bioreactors and associated liquid/gas handling system are connected to a utility tower, which is controlled by a controller. In this Figure the controller is configured using a HMI.
Figure 2B:
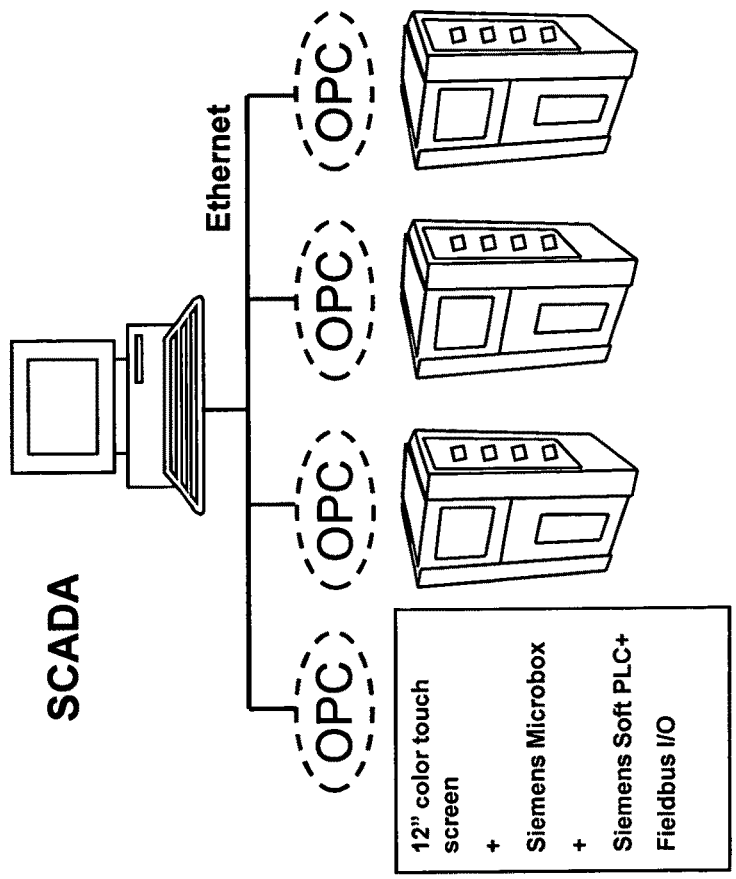
FIG. 2b shows a typical network architecture, where multiple utility towers are connected to a SCADA system using OPC and the Ethernet.
Figure 2A:
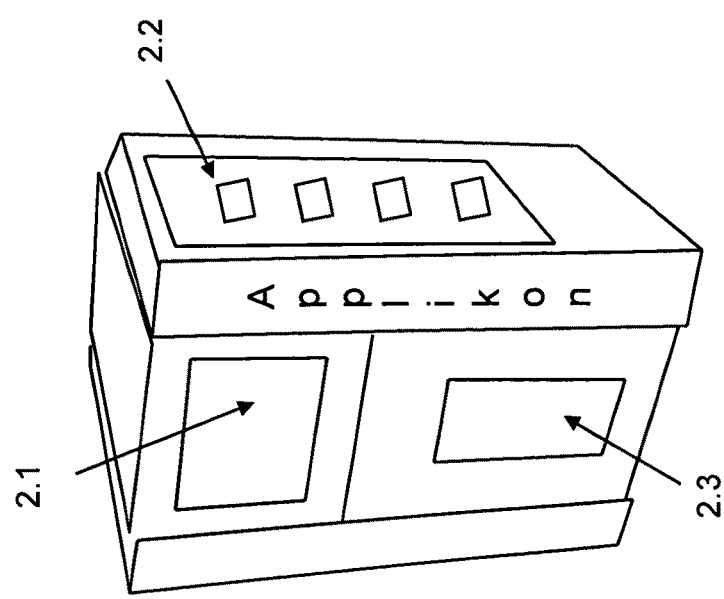
FIG. 2a shows a utility tower having integrated liquid/gas handling and HMI. This unit is capable of controlling two bioreactors.
Figure 6:
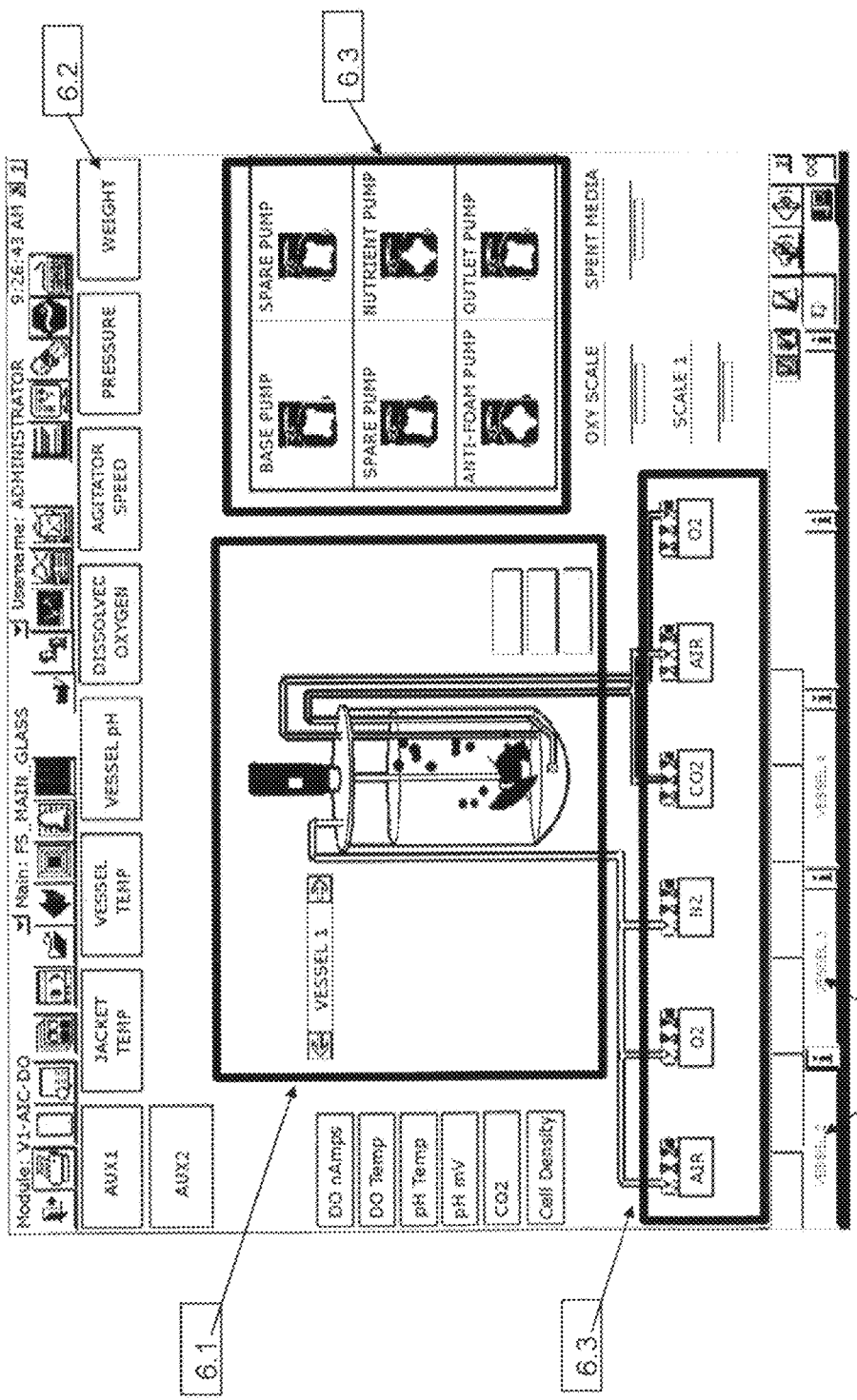
FIG. 6 shows an automation system HMI. The display provides an overview of the process, including the bioreactor configuration, associated hardware, control parameters and their corresponding set points.

As described above, a central or distributed prior art processing system like that shown in FIG. 1, which controls one or a plurality of bioreactors, is typically accompanied by an HMI. An intuitive yet capable HMI is important, so that attempts to simplify and optimize this interface have been made. The HMI interface is most often an interactive display on a computer monitor or a touch screen that is utilized to show the information required by a user to maintain control of the bio-process. FIG. 6 shows an example of a typical prior art bioprocess HMI for an autoclavable, glass vessel. The information displayed usually includes a graphical representation of the bioreactor 6.1, detailed control parameter values and any associated process set-points 6.2, primary system hardware components 6.3 (e.g. pumps, mass flow controller, scales), and also alarms and warnings 6.4.

Figure 7A:
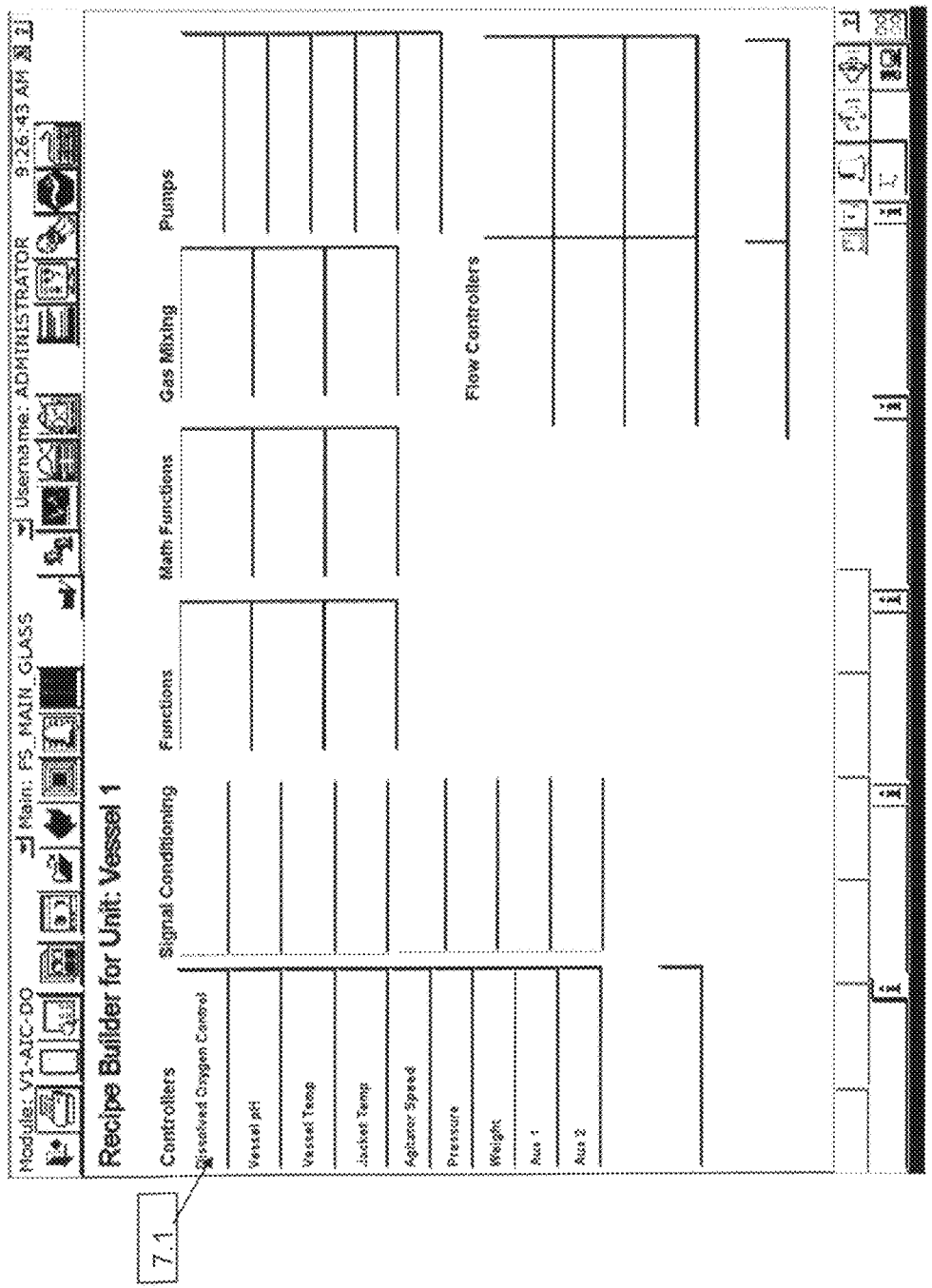
FIG. 7a shows a configuration page from an automation system HMI. The control parameters are enumerated and configuration windows can be used to set the control strategy.
Figure 7B:
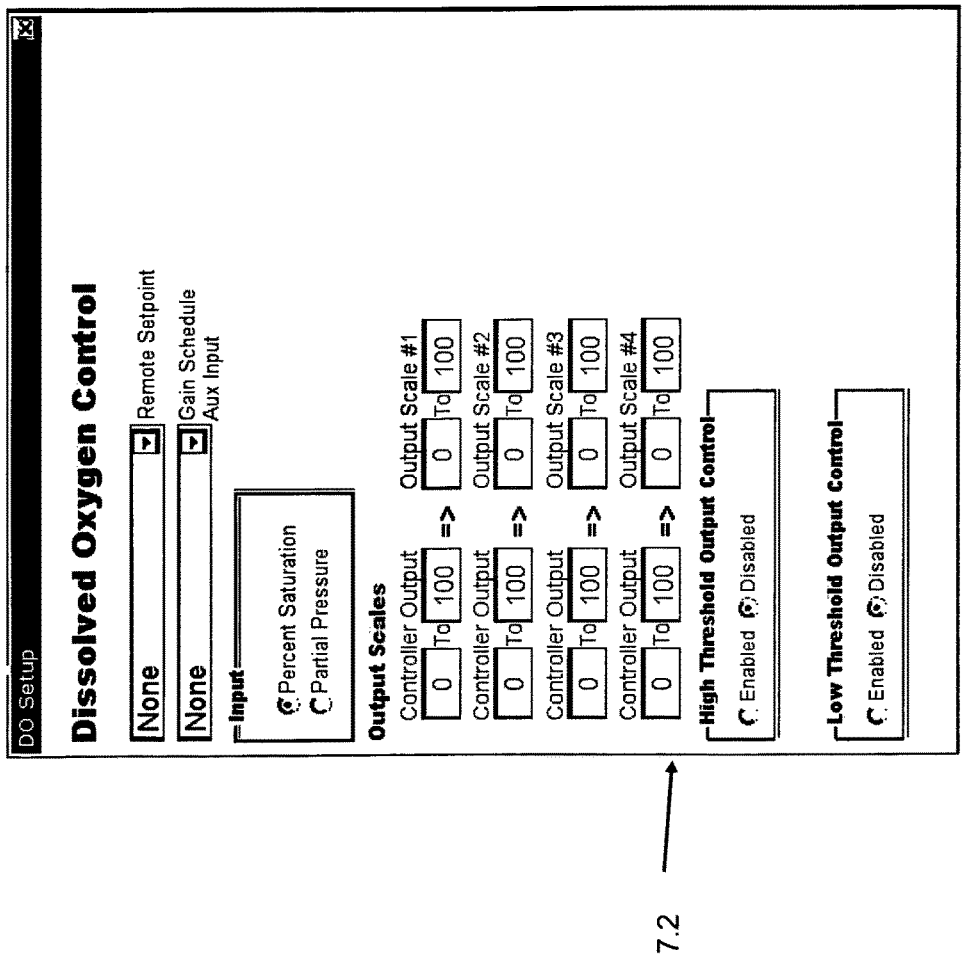

The HMI software usually has several different pages. FIG. 7a shows a typical "overview" page, where the user can see basic information about the configuration of each process vessel. FIGS. 7a and 7b show a typical configuration page of the HMI, where the bio-process engineer can set process parameters 7.1 and program control strategies and loops 7.2. In many automation systems, once the process strategy is set, the user can store all of the configuration and startup information in a file, for later upload, or propagation to other vessels. Many of these automation functions and display graphics have become commonplace in most automation HMI interfaces, so that a new user can learn to set up their process quickly.

Figure 7C:
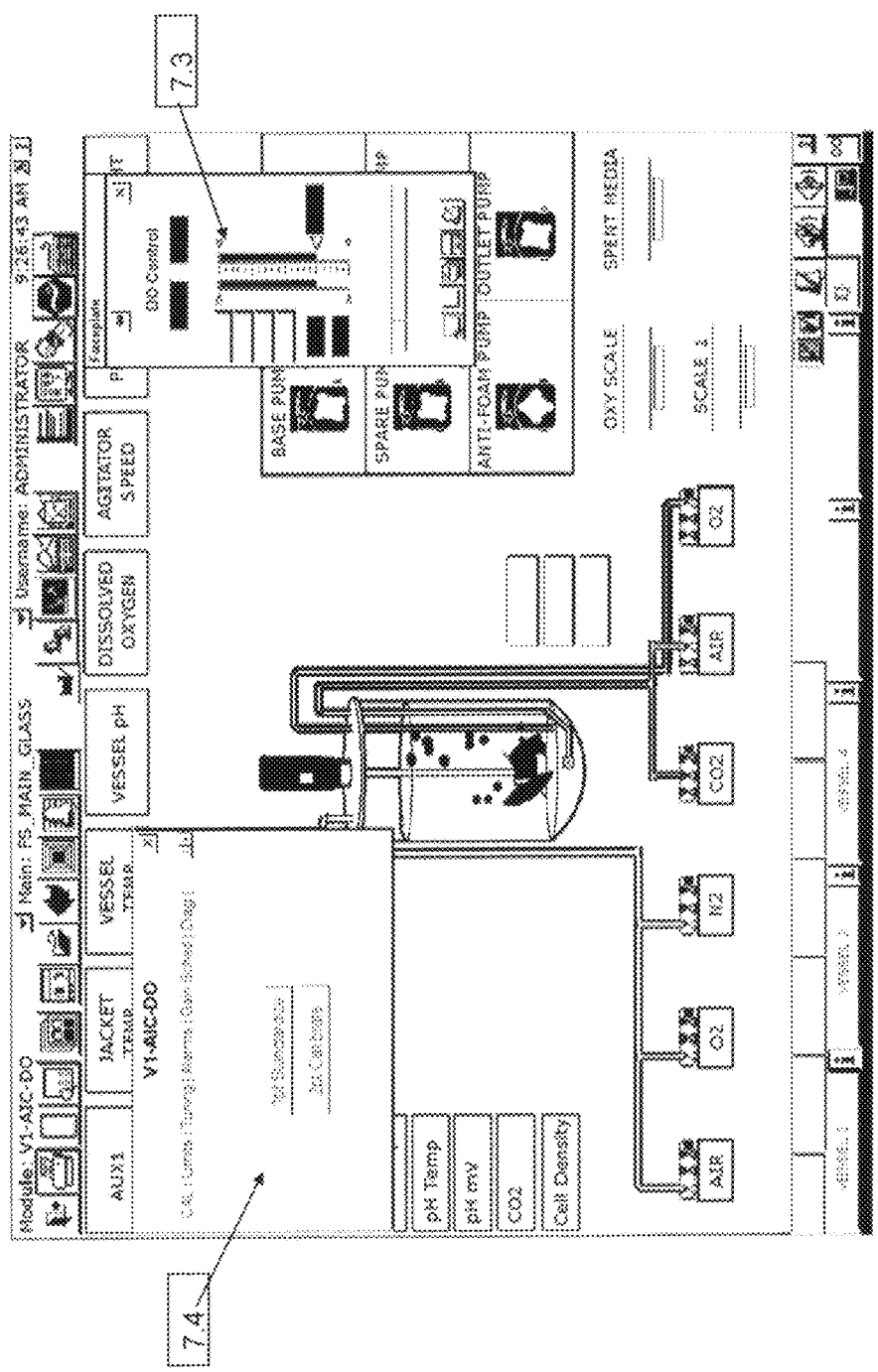
FIG. 7c shows a typical sensor page from an automation system HMI. The sensor has an associated parameter faceplate (shown in FIG. 7d), a command faceplate with tabs indicating the different functions, and separate windows displaying information about the sensor.

However, in prior art automation systems, the sensor transmitters are not readily physically accessible, therefore when using the HMI, the end user needs to learn how to use proprietary and unfamiliar interfaces. In the most extreme situation, either the transmitter electronics are so proprietary that the user must access the boards to change settings or calibrate the transmitter (e.g., with dip-switches or potentiometers), or the user has no access to the transmitter at all. In automation systems employing digital transmitters, the HMI (shown in FIGS. 7c and 7d) can contain a graphical 7.3, or tabular 7.4, "faceplate" which provides information about the sensor and transmitter data stream and settings. In some automation systems, the digital transmitter can be calibrated or its measurement its measurement standardized and the settings stored so that the user has a record of the sensor parameters that can be viewed in a calibration "window" 7.5. Such graphical HMI systems, although more capable than the menu-driven, generally less expensive automation systems, usually do not provide full access to all transmitter functions. They are also not as intuitive or easy for the user to learn, understand and use.

As manufacturers strive to reduce the cost of bioprocess control hardware while simultaneously maximizing the information obtained from a given bioreactor, it is desirable to eliminate any redundant components in the system design. In many cases, a significant fraction of a utility tower's component cost is represented by the digital transmitters. We have found that by using electronic cards (the printed circuit boards present inside the transmitter) having equivalent functionality to measure and transmit primary, secondary, and even tertiary process variables, as well as to receive calibration commands and/or perform diagnostic sequences, it is possible to replace the conventional digital transmitters and eliminate the significant cost of the transmitter packaging (e.g., enclosure, display, keypad, etc.). This allows for use of "non-dedicated" components, or more specifically components that serve multiple purposes as opposed to being dedicated to one specific function. For example, the keyboard associated with the HMI (a user input and information display device) can be used to input the temperature, pH, dissolved oxygen, dissolved $CO_2$, or any relevant analyte's information, as opposed to using a separate dedicated keyboard associated with each transmitter for each of the aforementioned sensors. The digital controller used in the bioprocess automation system of the present invention can replace the dedicated microprocessor used in each individual transmitter. In addition, if electronics boards are designed to communicate with a digital bus, then the need for a translator block is eliminated, leading to further simplification and cost savings.

The bioreactor monitoring and control system of the present invention utilizes only non-dedicated user input and information display devices, a digital controller and software, and therefore comprises:

i) one or more diagnostic sensor probes for measuring an operating condition in the bioreactor ii) means, such as an electric or fiber optic cable, for transmitting the diagnostic signal from the probe (or each of the probes) to iii) signal conditioning and communication electronics (a card or cards) which supply operating current and/or voltage to said probe and which convert the diagnostic signal into a format accessible by iv) a controller which directly receives the format converted signal from the card and transmits it to v) a monitor which includes software which enables the monitor to display the converted signal and also, when appropriate, to instruct the controller to implement changes in the operating conditions in the bioreactor vi) a software-based virtual transmitter which substantially replicates the keyboard, display, menu-tree and response of a physical sensor transmitter.

Figure 3B:
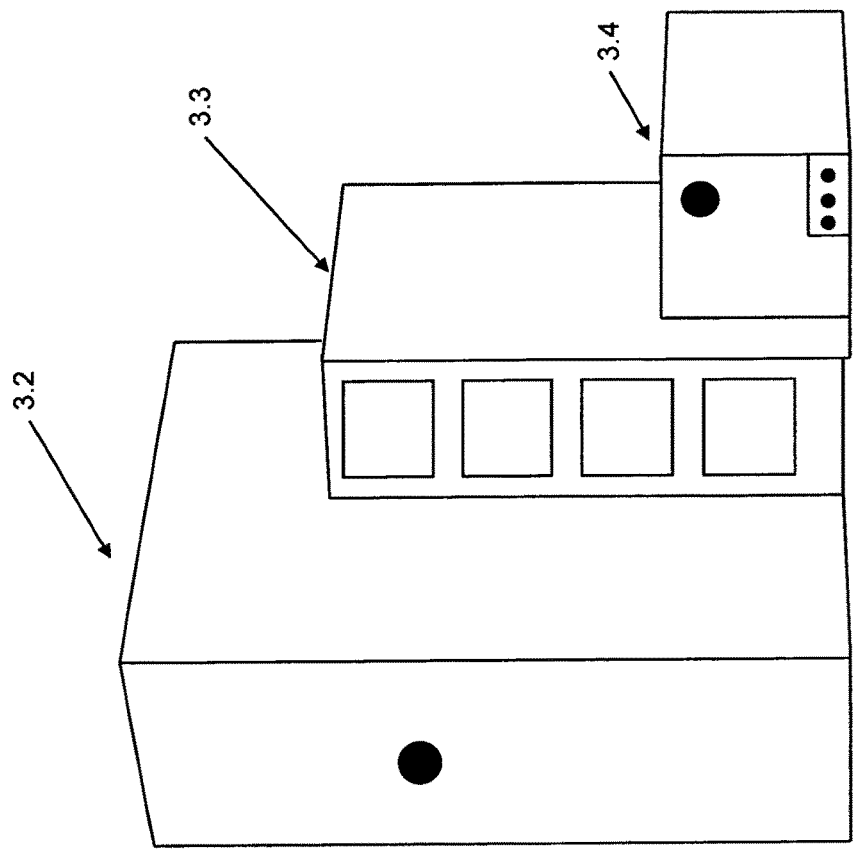
FIGS. 3a and 3b show a modular utility tower system where the liquid/gas handling and HMI are packaged separately. The utility tower now contains only sensor transmitters and signal translators and aggregators.
Figure 3A:
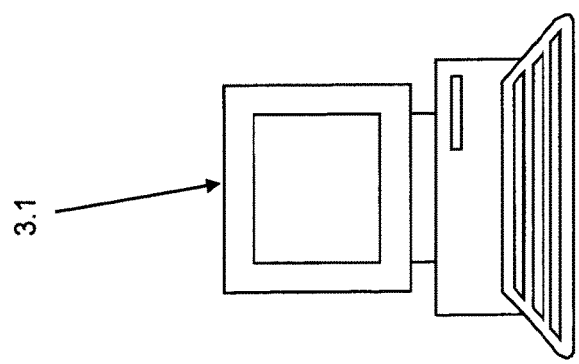
Figure 5:
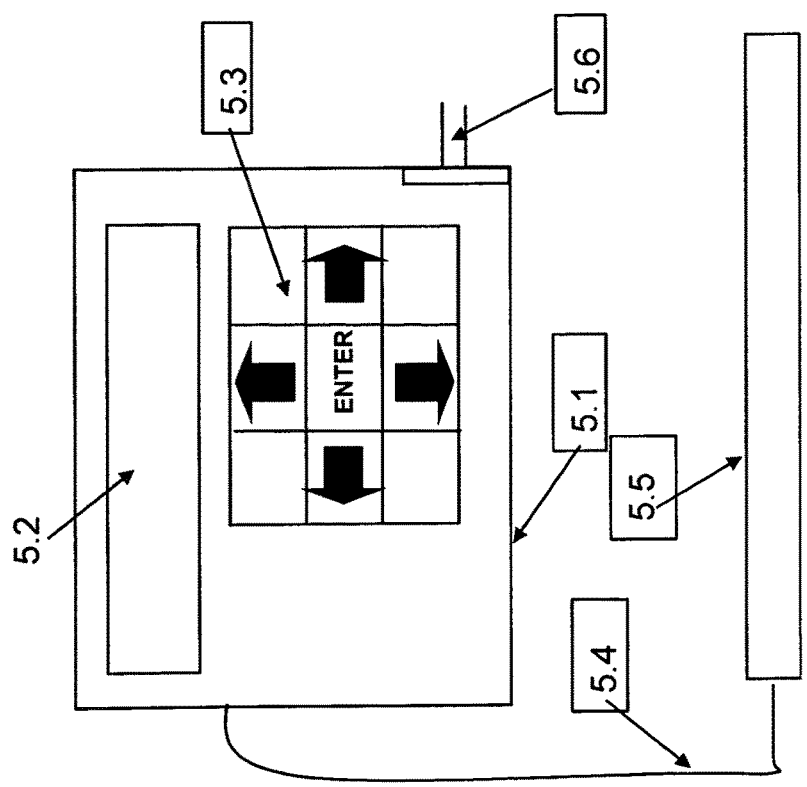
FIG. 5 is a schematic which shows a prior art transmitter connected to a sensor via a cable.

The software based virtual transmitter of the present invention therefore does not need a separate physical keyboard to enter data but it performs the function and action of a physical transmitter, and has equivalent measurement capability. Specifically referring to FIG. 5, the keyboards 5.3 shown on the physical transmitters are no longer necessary. Additionally, the entire case 5.1 holding the keyboard and the display 5.2 for this transmitter are entirely unnecessary as this functionality can be addressed by the bioreactor control systems HMI. Looking at FIG. 3a (3.1)_a keyboard and monitor is clearly shown where the display of Figure 9f would appear, including the virtual transmitter representation.

Figure 4:
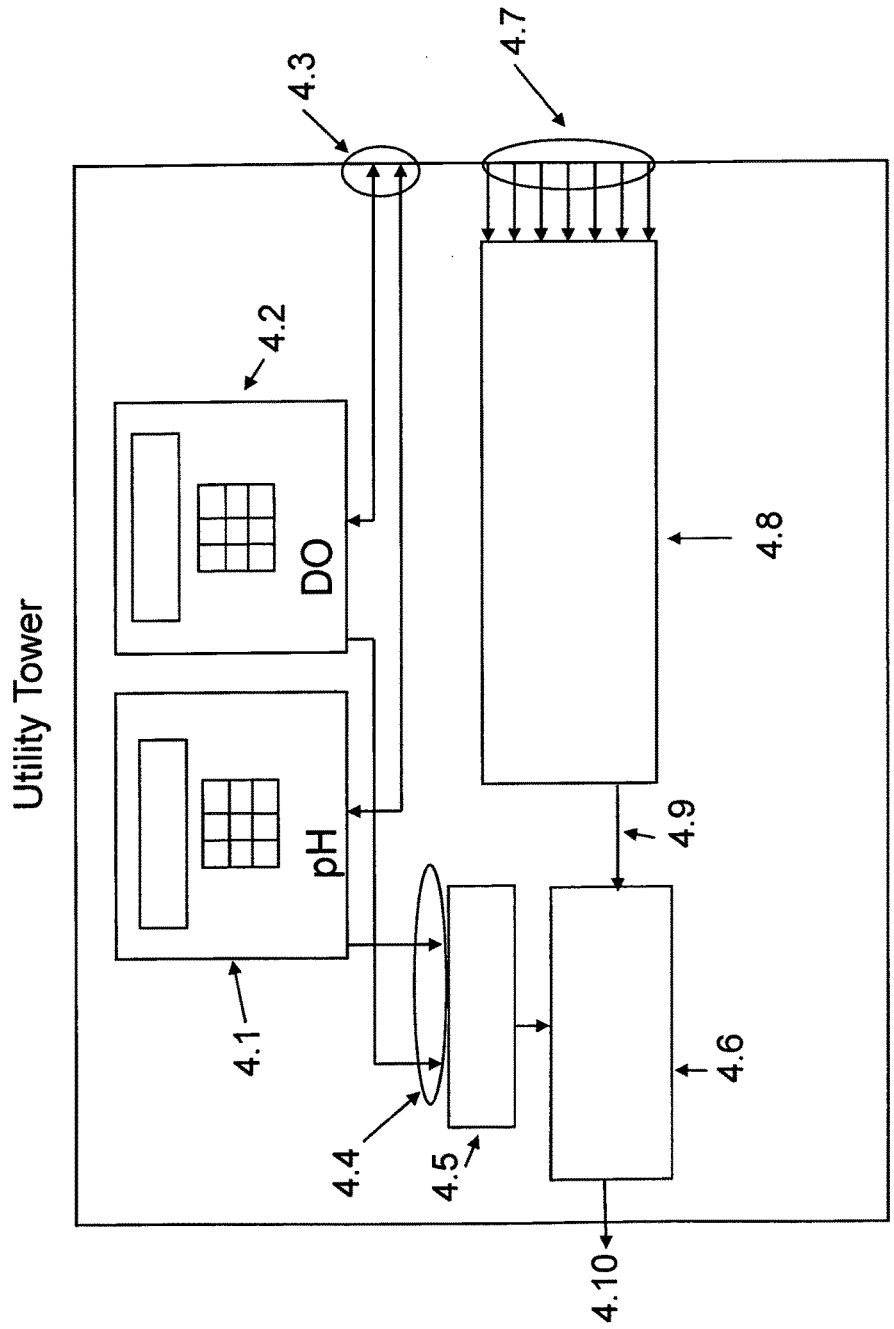
FIG. 4 is a schematic which shows the layout of a prior art utility tower containing transmitters, a translator for the transmitters to convert their output to a digital protocol, and signal aggregators.
Figure 8:
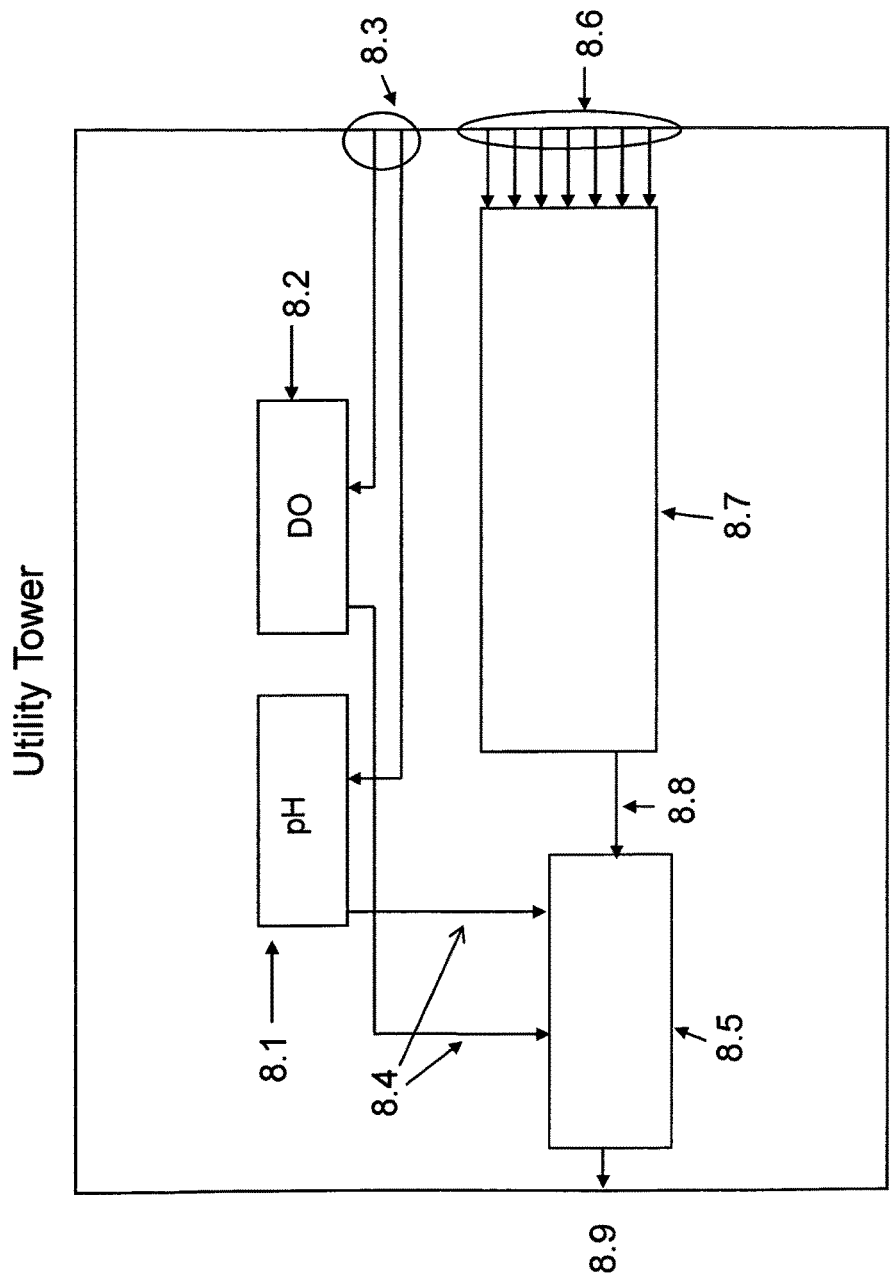
FIG. 8 shows the schematic layout of a utility tower in accordance with the present invention, where the transmitters have been replaced with electronic cards having the same functionality. The interface to the electronic card is now "virtual", through the HMI. The utility tower still contains signal translators and aggregators.

FIG. 8 shows how such electronic signal conditioning cards for pH 8.1 or dissolved oxygen (DO) 8.2, having the same functional capacity as a traditional transmitter, can be directly plugged into the utility (or transmitter) tower digital bus. Note that the cards still receive the sensor input via cables 8.3 and are directly connected 8.4 into the main signal aggregator 8.5. The translator has been eliminated from the utility tower, while the other analog/digital inputs 8.6 from other hardware such has pumps, scales, and agitator motors and their associated translator/aggregator 8.7 remain unchanged, and continue to provide additional input 8.8 into the main signal aggregator 8.5. The main signal aggregator's output 8.9 remains connected to the controller, as in FIG. 4. Thus, the utility tower architecture of the reduced cost system of the present invention shown in FIG. 8 is similar to the original utility tower architecture shown in FIG. 4, but the translator has been deleted, and the third party transmitters have been replaced with electronic cards that perform the same function, but which require no packaging or display. In this configuration, the HMI (e.g., a mouse or touch-screen) can be directly used to set-up the electronic card configuration, and also to calibrate/configure each sensor, as if using a physical transmitter.

Figure 9A:
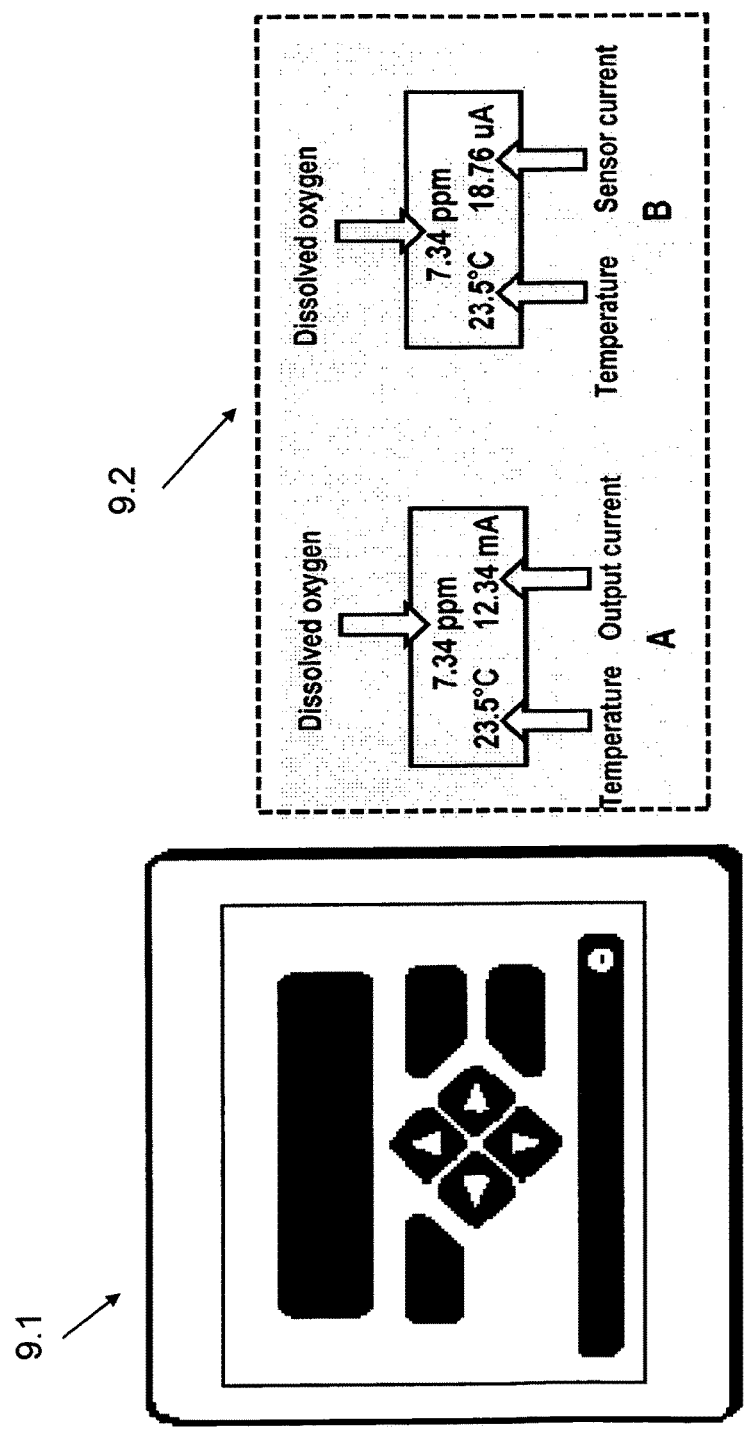
FIG. 9a shows a physical transmitter (9.1), and the display parameters (9.2) in accordance with the prior art.
Figure 9B:
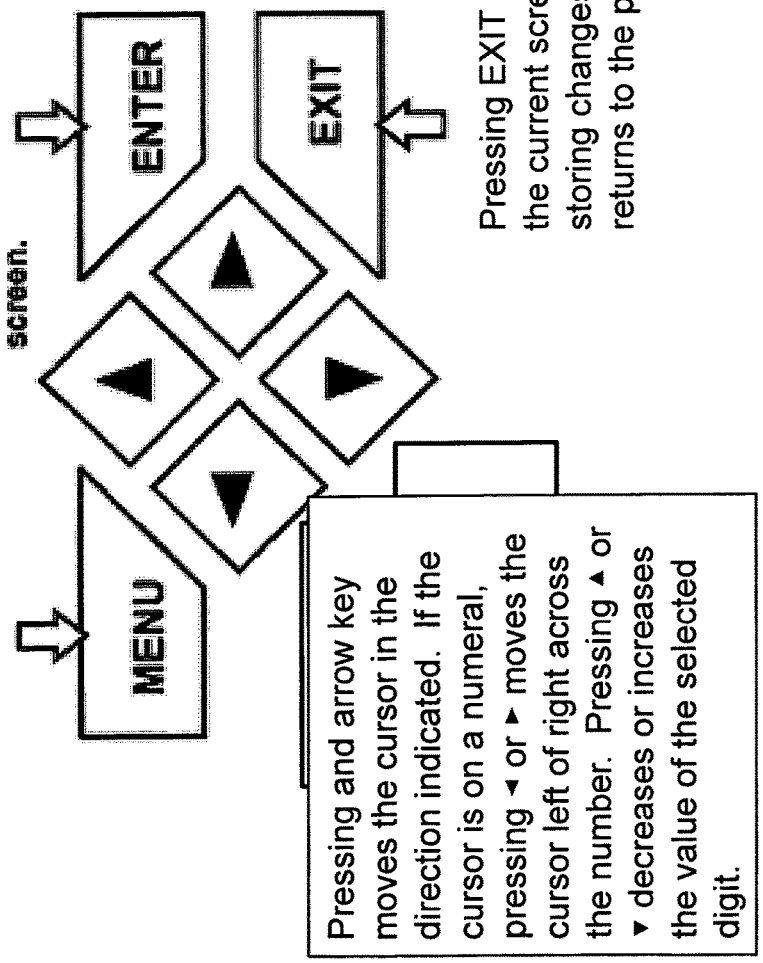
FIG. 9b shows keypad functions (9.3) for a physical transmitter.
Figure 9C:
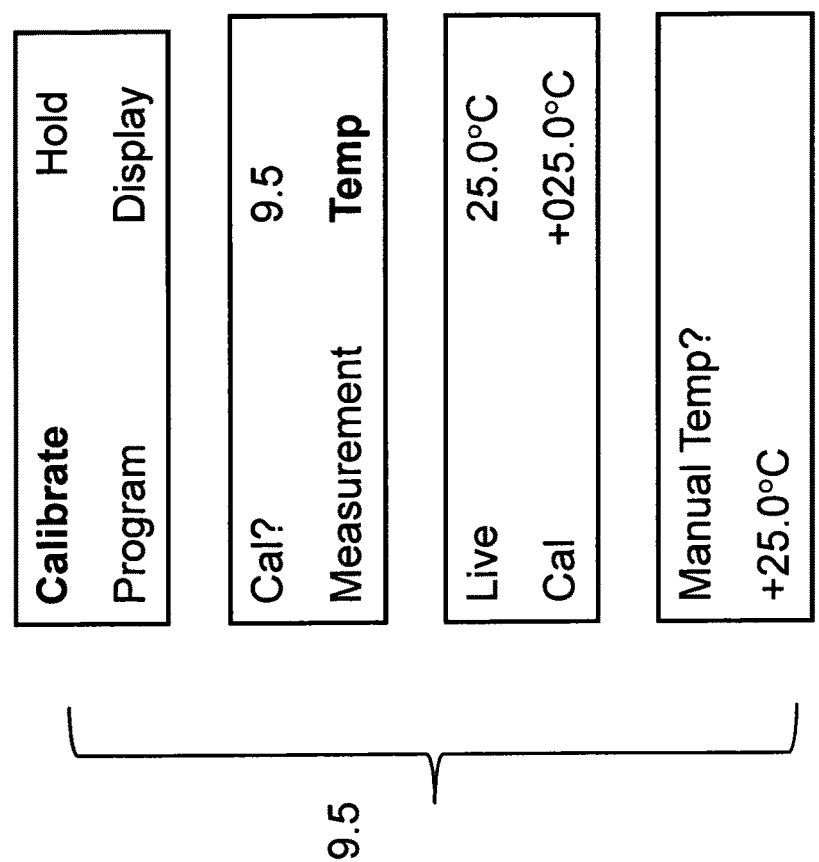
FIG. 9c shows a calibration display screen (9.5).
Figure 9D:
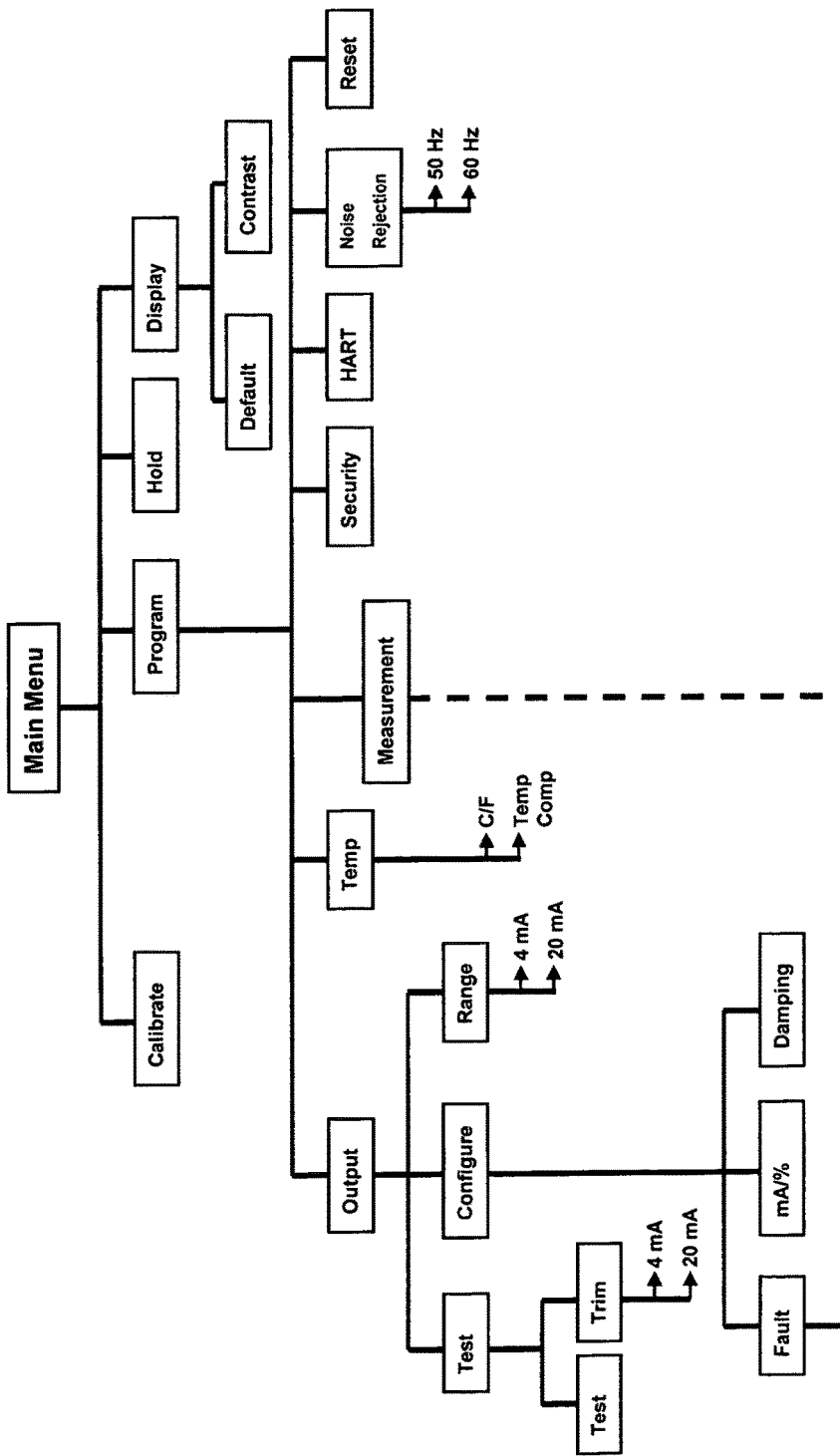
FIGS. 9d and 9e show menu trees for a dissolved oxygen transmitter in accordance with the prior art.
Figure 9E:
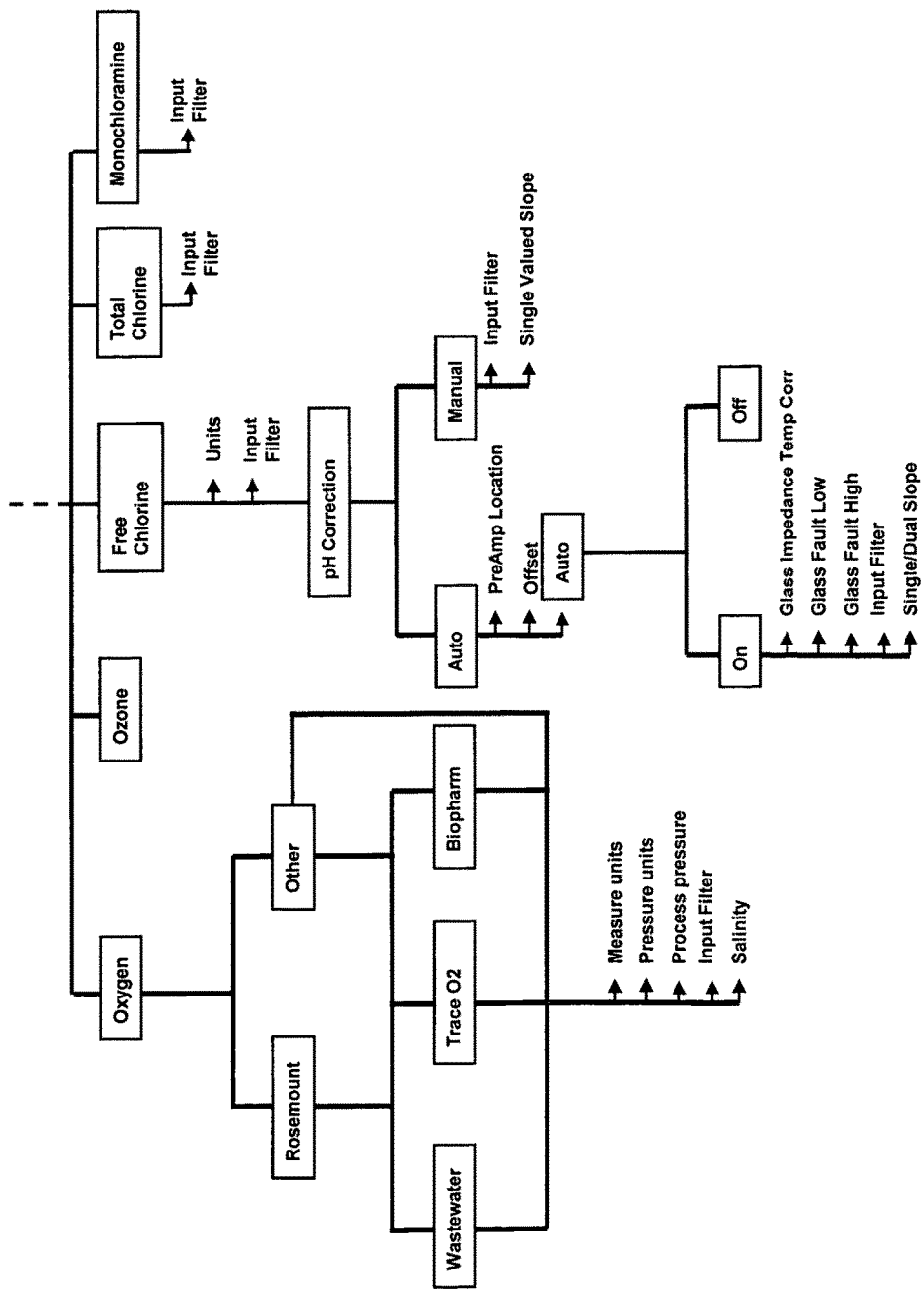
Figure 9F:
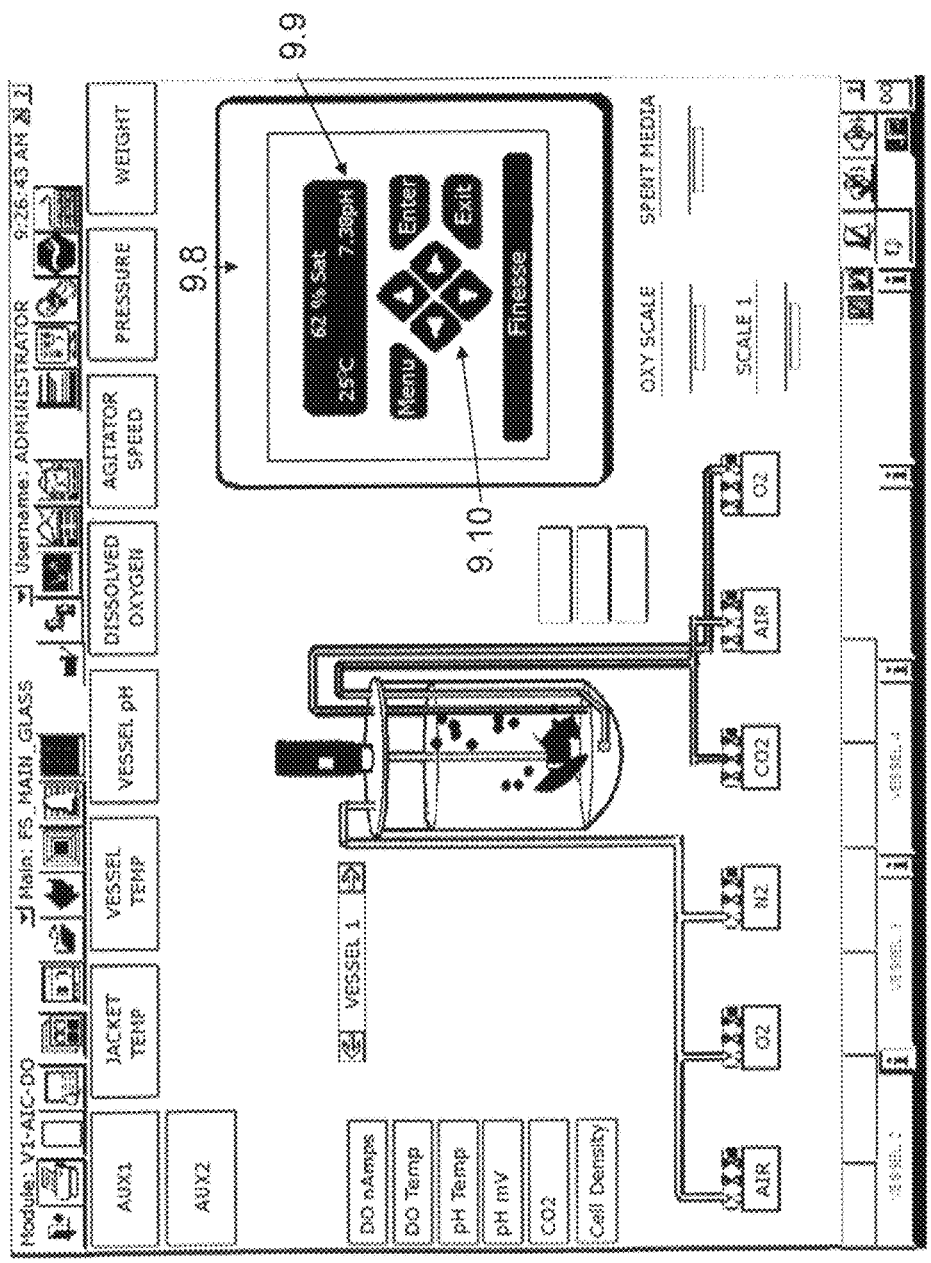
FIG. 9f shows a "virtual" transmitter in accordance with the present invention which mimics the display and keypad functions of the physical transmitter shown in FIGS. 9a, 9b, and 9c. This "virtual" transmitter will show the same or functionally equivalent display screens and have the same menu tree as the physical transmitter, but is implemented in the software of the HMI.

By using transmitter cards in the utility tower that have equivalent functionality to a transmitter such as is commonly used in the industry, it is possible to create a user interface for the HMI that effectively mimics the physical transmitter 9.1 shown in FIG. 9a. The concept of a "virtual" transmitter in accordance with the present invention is that the look and feel associated with the prior art, physical transmitter is mimicked by the HMI software and graphics. The functions of the original, physical transmitter are accessible through the HMI, without the need to open the utility tower to see a physical display 9.2 or punch commands into a physical keypad 9.3 of FIG. 9b, and without the cost of transmitter 9.1. The command sequences 9.5 in FIG. 9c are an example of temperature calibration of a DO sensor. The menu-tree in FIG. 9d and 9e is an example of a menu tree from a DO transmitter such as one made by Rosemount Analytical, and all associated features of a traditional transmitter can be implemented "virtually" within the HMI software of the automation system. FIG. 9f illustrates how such a "virtual" transmitter, in accordance with the present invention, can be implemented within the HMI from FIG. 7a to mimic a physical DO transmitter such as the one made by Rosemount Analytical. By clicking on the Dissolved Oxygen window, the user would active the "virtual" transmitter graphic 9.8. The simulated display screens 9.9 allows the user to read the data stream and display prompts from the "virtual" transmitter, while the simulated keyboard graphic 9.10 allows the user to enter data or commands into the "virtual" transmitter.

Thus, the "virtual" transmitter concept of the present invention allows the user to seamlessly transition from prior art physical transmitters with familiar commands, calibration procedures, and menu trees to the novel control system of the present invention which provides improved capability and self-monitoring, without having to learn a new transmitter interface, and without any ambiguity imposed by the HMI's interpretation of the transmitter operation. Moreover, because the "virtual" transmitter is implemented as a pure gateway for the transfer of sensor data into the control system, and since it does not itself store any of the data, it is not governed by 21 CFR part 11 requirements, and will therefore not affect the overall automation system's 21 CFR part 11 compliance.

Minimizing the validation required for a new technology is always a key factor in its adoption by the biopharmaceutical industry. A system must be able to be validated if it is to be used in research or process development, and then scaled into GMP applications. For the virtual transmitter, both the electronic cards and the software must be tested, and demonstrate substantially equivalent performance to the transmitters they are replacing. Specifically, the electronic cards used in the present invention provide performance and functionality substantially identical to those of the original transmitter, and this interchangeability can be readily demonstrated and documented with straightforward performance testing. Similarly, by mimicking the physical transmitter in the HMI as described previously and validating the software implementation for each "virtual" transmitter the automation system manufacturer can test and then provide essentially identical performance. The end result is that not only will the end user experience a seamless transition from the physical to the "virtual" transmitter, but any existing standard operating procedures (SOP) used by the end user in quality and validation documentation will remain unchanged. The requirement that a "virtual" transmitter mimic a traditional, physical transmitter enables an upgrade to existing automation system having traditional sensors and measurement methods. However, for new measurement methods or novel sensor designs, the virtual transmitter concept of the present invention can be implemented with greater capability and flexibility.

Figure 10A:
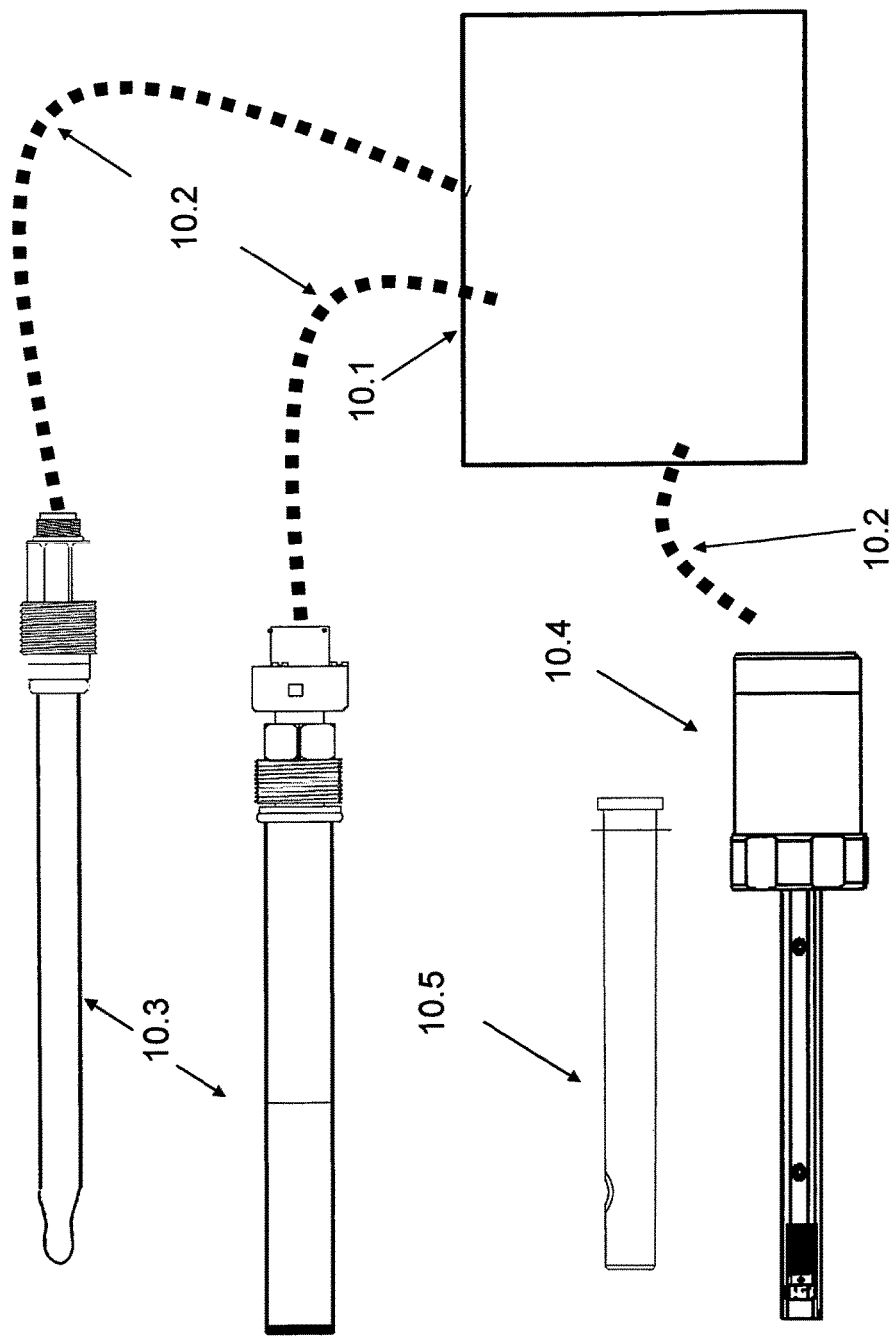
FIG. 10a shows a connection of traditional sensor output signals to the electronics card inside the utility tower in accordance with the present invention.

In the embodiment of the present invention described previously, and illustrated generally in FIGS. 8 and 9e, and in further detail in FIG. 10a a traditional transmitter is replaced by an electronic signal conditioning card 10.1 inside the utility tower of a bioreactor control system, and the HMI user interface is programmed to display a "virtual" transmitter image that mimics the display and command set of a physical transmitter. In this architecture, the sensor 10.3 still has no intelligence, but only transmits its raw output signals to its corresponding electronic card 10.1, e.g., using electrical cables 10.2. Similarly, disposable sensors having a "transducer" 10.4 that contains the optical/electrical elements necessary to measure the raw signal from a disposable element 10.5 inserted inside the process vessel, transmits the raw sensor output to a corresponding electronic card 10.1 using an electrical cable 10.2. Note that this concept can even be extended to fiber-optic based disposable or autoclavable sensors whose optics and electronics are housed on the electronic card 10.1 inside the utility tower, and where cable 10.2 is not an electrical cable but rather an optical fiber, and the sensor 10.3 is a physical adapter by which the end of the fiber is inserted inside the bioprocess vessel or is in contact with the active element (e.g., a fluorescent material). This concept can also be extended to systems where the fluid in the bioreactor itself is the active element (e.g.: when detection involves Raman scattering or NIR spectroscopy).

In the prior art configurations, if the type of sensor is changed or if additional redundancy is needed for a specific measurement, then the utility tower must be opened and the physical electronic card configuration must be modified accordingly. Such physical changes to the hardware either require the electronic cards to be "hot-pluggable" by the end user, or alternatively require the end user to call a field service or in-house automation engineer/technician to make the hardware change. In all cases, the automation system must be powered down, so that changes can only be made in between growth runs, and usually need to be scheduled. Furthermore, a re-calibration of all sensors must be executed after the hardware change, to ensure that the physical cards and sensors work together correctly, resulting in additional time and labor costs. In GMP applications, if the hardware is modified, the corresponding changes must be set in the input/output modules of the automation system, and the new system re-validated and re-tested, which leads to yet additional labor and schedule delays.

Figure 10B:
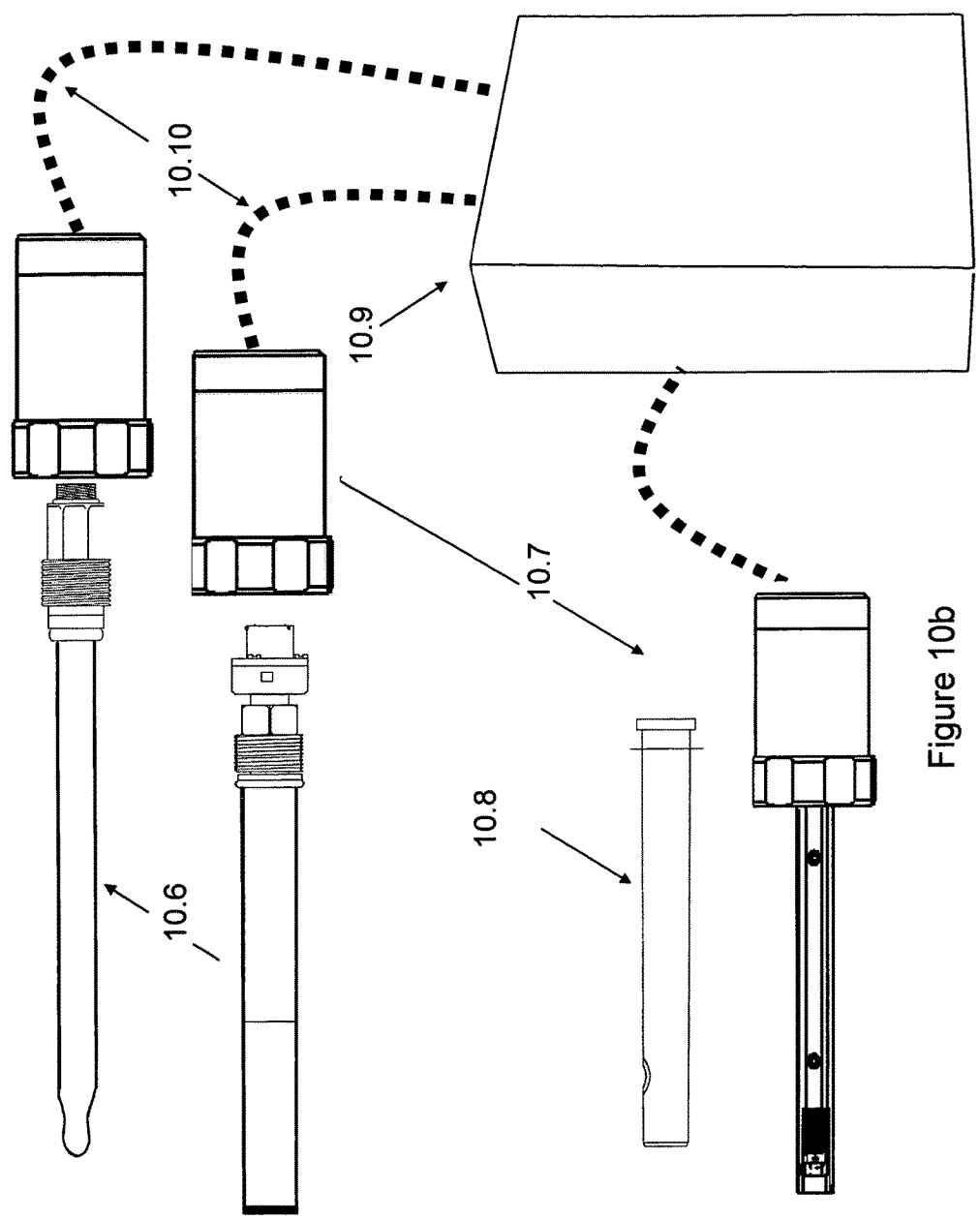
FIG. 10b shows the connection of either traditional or new sensors through "readers" that replace the electronic card in the utility tower. The outputs of the sensors are now either standard analog signals (with no diagnostics) or digital bus signals (with full diagnostics). These sensors are "hot-pluggable" to the utility tower.

In order to resolve these limitations, and make the sensors "hot-swappable" or configurable "on-the-fly", the electronic card functionality must be moved outside of the utility tower and closer to the sensor, as shown in FIG. 10b. For traditional sensors 10.6, the electronic card can be miniaturized and packaged inside "reader" 10.7 that locks onto the sensor's connector. The output of "reader" 10.7 is a digital bus protocol, such as Modbus, Foundation Fieldbus, DeviceNet, or ProfiBus, so that the reader is connected with the utility tower 10.9 by means of a standard bus interface cable 10.10. For new types of sensors, such as optical or disposable sensors 10.8, the "transducer" and transmitter electronics can suitably be integrated into the "reader" 10.7. The output of "reader" 10.7 for the new sensor would also be a digital bus protocol. Note that cables 10.10 would all be identical (for a same bus protocol) and be independent of the sensor type, whereas cables 10.2 depend on the connector type of the sensor, and would vary from sensor to sensor.

The sensor signals on cables 10.2 in FIG. 10a are most frequently analog, whereas the signals on sensor cables 10.10 in FIG. 10b are digital, so that their transmission is more robust and immune to noise ingress. Furthermore, cables 10.10 carry information about the sensor reading as well as sensor identification, diagnostics, and calibration data. Note that with further miniaturization, the "reader" electronics can be integrated directly into the sensor body, so that the sensor 10.6 can be connected directly to cable 10.10.

In the design configuration of FIG. 10b, the sensors are hot-swappable, so that new or redundant sensors can be added to the utility tower at any time, because the automation system can extract the necessary information from the sensor "reader". If communications standards are set for the bus interface and "reader" commands, such a system could be tested and validated by the manufacturer for a group of pre-approved sensors, both internally designed or from third party manufacturers. The end user can then change the sensor configuration automatically, and without the need to re-validate the hardware and software automation systems.

Figure 11:
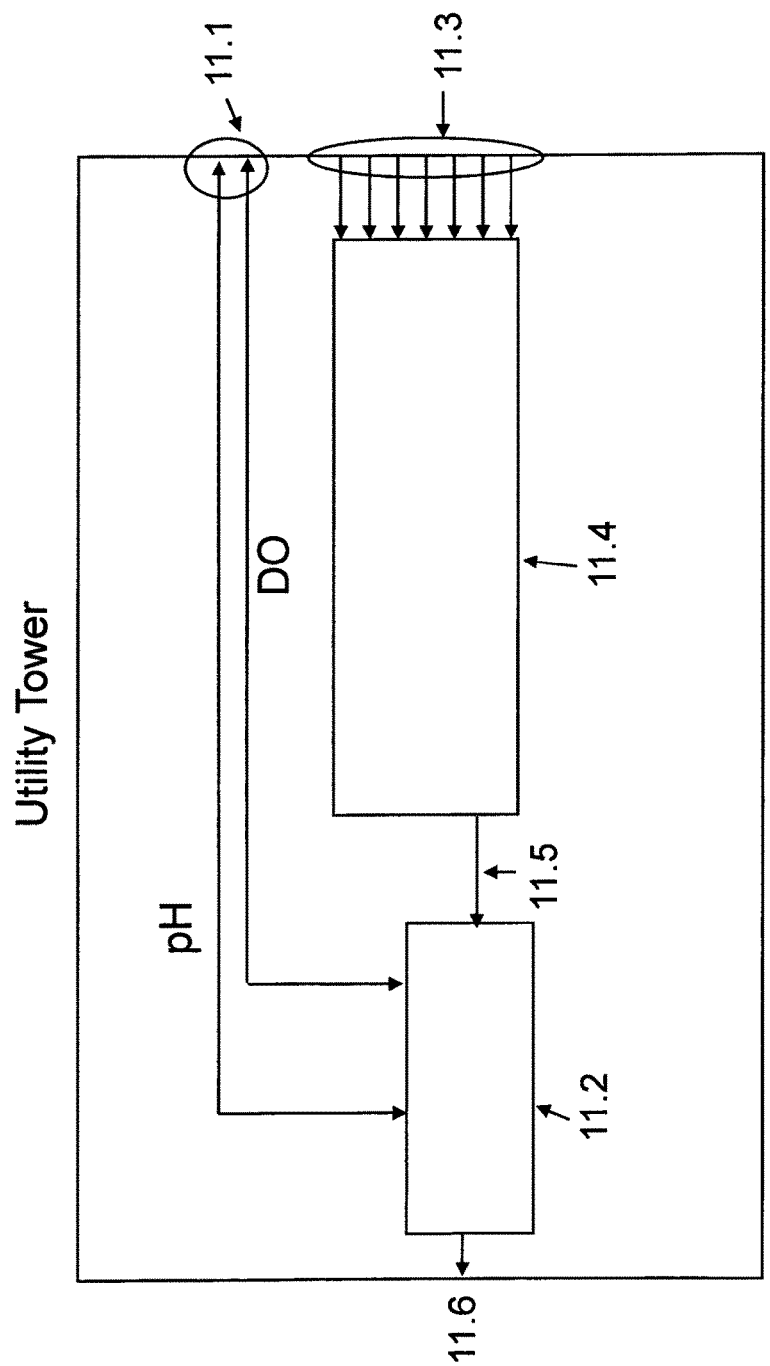
FIG. 11 is a schematic in accordance with the present invention which shows the layout of a utility tower where the electronic card functionality is implemented outside of the utility tower and inside either a sensor reader or the sensor probe itself. The interface to the sensor is "virtual", through the HMI. The utility tower still contains signal translators and aggregators.

FIG. 11 demonstrates how the digital "readers" can provide inputs 11.1 directly into the main signal aggregator 11.2 inside the utility tower. This design allows for the control system to rapidly identify and communicate with each sensor and obtain a full set of sensor calibration data and diagnostics. The other signals from the analog and digital aggregator/translator 11.4 reach the main signal aggregator 11.2 by connector 11.5, and would be merged with the sensor digital signals 11.1 prior to output 11.6 to the controller and automation system.

Note that if diagnostics and calibration are not required, a simpler and less expensive version of the sensor "reader" can be implemented. In this embodiment, the "reader" would measure the raw sensor readings and transmit them either as a standard analog (4 to 20 mA) or digital (0 to 10 V) signal, without the full bus communications protocol. In this case, cables 10.10 would suitably be standard two-wire cables, rather than digital bus cables, and the sensor output 11.3 could enter the analog and digital aggregator/translator 11.4 inside the utility tower.

In yet another embodiment of the present invention, the electronics of an optical sensor, such a fluorescence-based pH or dissolved oxygen sensor, can mimic the sensor output of a traditional electrochemical or polarographic sensor, respectively, and provide their output to the same "reader" 10.7 employed by traditional electrochemical probes. For example, the electronics inside the sensor could transform the optical signal into a voltage output (mV) for the optical pH sensor, and into a current output (40 to 80 nA) for the dissolved oxygen sensor. By using the same connector (e.g., VP-style) on the optical sensor, it could directly replace the traditional sensor in this architecture.

In the above scenario, it is also possible to use the electronics in the probe to allow the user to perform the calibration at the probe, and then use the cards in the bioprocess automation system to simply and/or further condition the signals. For instance with a dissolved oxygen probe, the user would follow the typical calibration path of putting the probe in two different known environments (e.g.: 0% oxygen and 100% water saturated air) and have the values recorded by the probe. The electronics and software in the probe would then be used to create the detailed connection between the two values, so that the probe is consistent and accurate.

Figure 12:
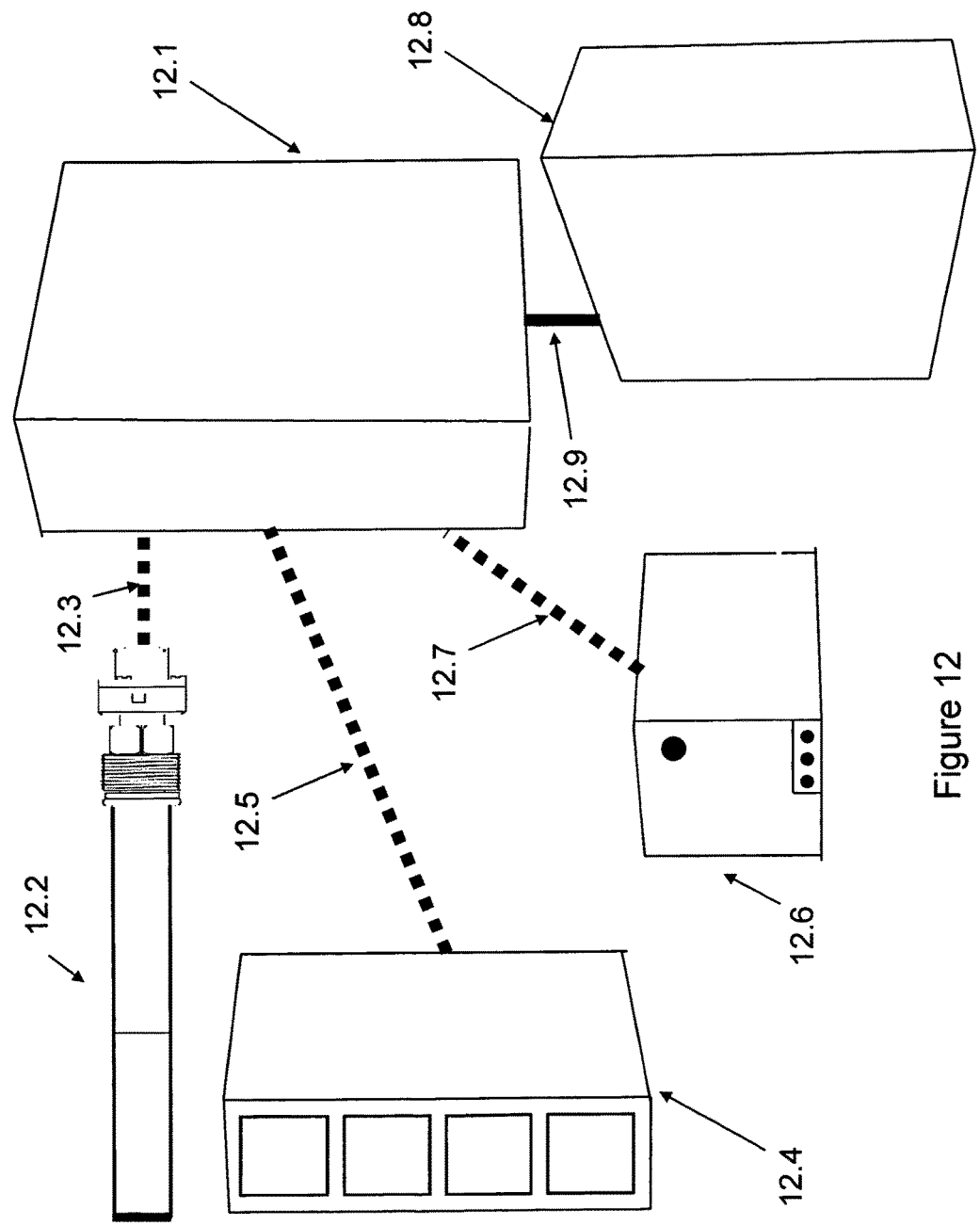
FIG. 12 shows a bioreactor control system in accordance with the present invention that is fully digital. The sensors, pump tower, and gas manifold all connect to the utility tower using cables that carry digital bus communications. The utility tower is connected to the controller using the same digital bus protocol. In this design, the transmitter functionality is contained within the sensor (i.e., is distributed), and the utility tower provides an aggregator for all of the digital signals.

FIG. 12 shows a schematic of a system in accordance with the present invention having digital sensors with readers directly integrated into the sensor shaft (or body). In this design, the transmitter functionality is contained within each sensor, and the utility tower simply provides an aggregator for all of the digital signals. Utility tower 12.1 can be connected to "hot-pluggable" sensors 12.1 with electrical cables 12.3, much in the same way as it would be connected to a pump tower 12.4 using cable 12.5 or a gas manifold 12.6 using cable 12.7. The utility tower can then be connected using cable 12.9 to the controller cabinet 12.8. The controller cabinet can be connected to the supervisory PC as well as additional HMI workstations. Note that this system can be designed so that cables 12.3, 12.5, and 12.7 are all digital bus cables, and the sensors and actuator towers (pump tower 12.4 and gas manifold 12.6) all employ the same digital bus protocol. The functionality of the utility tower would then be reduced to providing signal aggregation to the controller.

In this approach, the functionality of the original transmitters inside the utility tower has been transferred to the sensors themselves. The cost of the transmitter function is significantly reduced because the transmitter enclosure, display, and keypad are eliminated. Furthermore, if all of the sensors employ the same digital protocol and same menu tree, then the cost of programming and validating of each transmitter is reduced, so that the engineering and quality check-out (validation) costs of developing the utility tower are lower, and allow for more competitive pricing of the final product.

We claim:

1. A bioreactor monitoring system comprising:
   i) at least one in situ diagnostic sensor probe for measuring operating conditions in a bioreactor,
   ii) an electronic card comprising signal conditioning and communication electronics for supplying operating current and/or voltage to said at least one diagnostic sensor probe, and converting the format of each signal generated from the at least one diagnostic sensor probe, and
   iii) a digital controller comprising a non-transitory computer-readable medium, the medium comprising instructions for running
   iv) a non-dedicated user input and information display device to present,
      a) a non-dedicated human machine interface, and
      b) a software-based virtual transmitter comprising simulated graphics which substantially replicate the keyboard, display, menu-tree and response of a physical sensor transmitter,
         wherein the virtual transmitter is configured to be displayed on the non-dedicated human machine interface,
         wherein the virtual transmitter is configured to show the converted signal,
         wherein the virtual transmitter is associated with the at least one diagnostic sensor probe, and
         wherein the electronic card interfaces to the software based virtual transmitter to enable the virtual transmitter and the electronic card to perform the function and action of the physical sensor transmitter.

2. The bioreactor monitoring system of claim 1 wherein the signal conditioning and communication electronics includes means for transmitting the diagnostic sensor probe signal.

3. The bioreactor monitoring system of claim 1 further comprising a utility tower wherein said electronic card is situated outside utility tower and said sensor probe is configured to be hot swappable into said utility tower.

4. A bioreactor monitoring system in accordance with claim 3 wherein the electronic card is configured to provide digital signals from each sensor probe to the utility tower.

5. The bioreactor monitoring system of claim 1 wherein the functions of the physical sensor transmitter capable of being performed by the electronic card and said virtual transmitter are accessible using the non-dedicated human machine interface.

6. The bioreactor monitoring system of claim 1 wherein said virtual transmitter is configured to measure at least one of the following bioreactor process parameters: pH, dissolved oxygen, temperature or dissolved carbon dioxide.

7. The bioreactor monitoring system of claim 1 further comprising a utility tower having said electronic card situated therein.

8. A bioreactor monitoring system in accordance with claim 7 wherein said utility tower contains signal aggregators.

9. A bioreactor monitoring system in accordance with claim 7 wherein said utility tower is connected to the digital controller using a digital bus protocol.

10. The bioreactor monitoring system of claim 1 wherein the virtual transmitter includes means for both transmitting process variables and receiving calibration commands.

11. A bioreactor monitoring system in accordance with claim 1 wherein the electronic card both sends diagnostic signals to and receives diagnostic signals from the probe.

12. A bioreactor monitoring system in accordance with claim 1 wherein said electronic card is situated inside the sensor probe.

13. A bioreactor monitoring system in accordance with claim 1 further comprising a fiber optic cable for transmitting a signal generated by said diagnostic sensor probe to the electronic card.

14. The bioreactor monitoring system of claim 1 wherein the virtual transmitter is configured not to store data from the converted signal.

* * * * *